United States Patent
Yin et al.

(10) Patent No.: US 9,139,796 B2
(45) Date of Patent: Sep. 22, 2015

(54) METHODS OF AND FORMULATIONS FOR REDUCING AND INHIBITING THE GROWTH OF THE CONCENTRATION OF MICROBES IN WATER-BASED FLUIDS AND SYSTEMS USED WITH THEM

(75) Inventors: Bei Yin, Buffalo Grove, IL (US);
Jingjun Yang, Round Lake, IL (US);
Pierre Marie Lenoir, Richterswil (CH)

(73) Assignee: Dow Global Technologies LLC, Midland, MI (US)

( * ) Notice: Subject to any disclaimer, the term of this patent is extended or adjusted under 35 U.S.C. 154(b) by 964 days.

(21) Appl. No.: 12/669,667

(22) PCT Filed: Jul. 21, 2008

(86) PCT No.: PCT/US2008/070651
§ 371 (c)(1),
(2), (4) Date: Jul. 20, 2010

(87) PCT Pub. No.: WO2009/015088
PCT Pub. Date: Jan. 29, 2009

(65) Prior Publication Data
US 2010/0286096 A1 Nov. 11, 2010

Related U.S. Application Data

(60) Provisional application No. 60/951,614, filed on Jul. 24, 2007.

(51) Int. Cl.
*C10M 173/00* (2006.01)
*A01N 57/20* (2006.01)
*C02F 1/50* (2006.01)
*C09D 5/14* (2006.01)
*C10M 141/10* (2006.01)
*C02F 5/00* (2006.01)

(52) U.S. Cl.
CPC .............. *C10M 173/00* (2013.01); *A01N 57/20* (2013.01); *C02F 1/50* (2013.01); *C09D 5/14* (2013.01); *C10M 141/10* (2013.01); *C02F 5/00* (2013.01); *C02F 2301/08* (2013.01); *C02F 2303/08* (2013.01); *C10M 2207/08* (2013.01); *C10M 2215/16* (2013.01); *C10M 2215/202* (2013.01); *C10M 2215/22* (2013.01); *C10M 2215/225* (2013.01); *C10M 2219/104* (2013.01); *C10M 2223/06* (2013.01); *C10N 2230/16* (2013.01); *C10N 2240/40* (2013.01)

(58) Field of Classification Search
CPC .................................................. C10M 173/00
See application file for complete search history.

(56) References Cited

U.S. PATENT DOCUMENTS

| | | | |
|---|---|---|---|
| 5,385,896 A | 1/1995 | Bryan et al. | |
| 5,670,055 A | 9/1997 | Yu et al. | |
| 5,741,757 A | 4/1998 | Cooper et al. | |
| 6,784,168 B1 | 8/2004 | Jones et al. | |
| 2001/0034366 A1 | 10/2001 | Beilfuss et al. | |
| 2003/0092584 A1 | 5/2003 | Crews | |
| 2003/0228373 A1 | 12/2003 | Ludensky et al. | |
| 2004/0082473 A1 | 4/2004 | Beilfuss et al. | |
| 2004/0087448 A1 | 5/2004 | Smith et al. | |
| 2004/0102501 A1 | 5/2004 | Lutz et al. | |
| 2008/0004189 A1* | 1/2008 | Smith et al. | 507/129 |

FOREIGN PATENT DOCUMENTS

| | | |
|---|---|---|
| EP | 0209260 | 1/1987 |
| EP | 0 385 801 A1 | 9/1990 |
| EP | 385801 A1 * | 9/1990 |
| EP | 1 402 778 A1 | 3/2004 |
| EP | 1402778 A1 * | 3/2004 |
| JP | 3041009 A | 2/1991 |
| JP | 11071213 A | 3/1999 |
| JP | 11222408 A | 8/1999 |
| JP | 2000-290112 A | 10/2000 |
| WO | WO9613502 | 5/1996 |
| WO | 03/062149 A2 | 7/2003 |
| WO | 2004/017736 A1 | 3/2004 |
| WO | WO2004113236 | 12/2004 |
| WO | 2005/074688 A2 | 8/2005 |
| WO | WO2009/015089 | 1/2009 |

OTHER PUBLICATIONS

EPA fact sheet. "4,4-Dimethyloxazolidine" 1996.*
Database WPI Week 199943 Thomson Scientific, London, GB; AN 1999-512415 XP002546000 & JP 11 222408 A (Katakura Kagaku Kogyo Kenkyusho KK) Aug. 17, 1999.
"Bioban CS-1135" [Online] (Oct. 10, 2002), DOW, XP002545999 Retrieved from the Internet: URL:http://www.dow.com/biocides/prod/bbcs1135.htm> [retrieved on Sep. 16, 2009].
"Bioban CS-1246" [Online] (Oct. 10, 2002), DOW, XP002513771 Retrieved from the Internet: URL:http://www.dow.com/biocides/prod/bbcs1246.htm> [retrieved on Sep. 16, 2009].
Database WPI Week 199921 Thomson Scientific, London, GB; AN 1999-248392 XP002546071 & JP 11 071213 A (Katakura Kagaku Kogyo Kenkyusho KK) Mar. 16, 1999.
PCT International Search Report and Written Opinion, PCT International Application No. PCT/US/2008/070651, mailed Oct. 5, 2009.

(Continued)

*Primary Examiner* — Paul Zarek
(74) *Attorney, Agent, or Firm* — McDonnell Boehnen Hulbert & Berghoff LLP

(57) ABSTRACT

The present invention provides methods and formulations for reducing or inhibiting increase in the concentration of microbes in a water-based fluid. The methods and formulations of the present invention use an oxazolidine compound and a hydroxymethyl-substituted phosphorus compound selected from the group consisting of tetrakis(hydroxymethyl)phosphonium salts, $C_1$-$C_3$ alkyl- and alkenyltris(hydroxymethyl)phosphonium salts and tris(hydroxymethyl)phosphine. The methods and formulations of the present invention can be useful in treating water contaminated with aerobic or anaerobic bacteria in oilfield and other industrial applications.

17 Claims, No Drawings

(56) References Cited

OTHER PUBLICATIONS

PCT International Search Report and Written Opinion, PCT International Application No. PCT/US/2008/070652, mailed Oct. 6, 2009.
U.S. Appl. No. 12/669,657, Methods of and Formulations for Reducing and Inhibiting the Growth of the Concentration of Microbes in Water-Based Fluids and Systems used with Them, filed Jan. 19, 2010.
U.S. Appl. No. 12/669,657, Office Action mailed Jul. 20, 2012.
U.S. Appl. No. 12/669,657, Office Action mailed Jan. 23, 2013.
Notice of Reasons for Rejection, Japanese Patent Application No. 2010-518320, mailed Jan. 22, 2013.
de Groot et al., Formaldehyde-releasers: relationship to formaldehyde contact allergy. Metalworking fluids and remainder. Part 1, Contact Dermatitis Jan. 17, 2010: 63: 117-128, 125.
Dow Product Safety Assessment for BIOBAN™ CS-1135 Antimicrobial, available at http://msdssearch.dow.com/PublishedLiteratureDOWCOM/dh_07e2/0901b803807e2c3d.pdf?filepath=productsafety/pdfs/noreg/233-00814.pdf&fromPage=GetDoc, 2011.
W. Paulus, "Directory of Microbicides for the Protection of Materials—A Handbook", pp. 462-63, 500, 2005.

\* cited by examiner

METHODS OF AND FORMULATIONS FOR REDUCING AND INHIBITING THE GROWTH OF THE CONCENTRATION OF MICROBES IN WATER-BASED FLUIDS AND SYSTEMS USED WITH THEM

CROSS-REFERENCE TO RELATED APPLICATIONS

This application is a U.S. National Phase of International Application No. PCT/US2008/070651, filed on Jul. 21, 2008, which claims the benefit of priority to U.S. Provisional Patent Application No. 60/951,614, filed Jul. 24, 2007, all of which are incorporated herein by reference in their entirety herein.

BACKGROUND OF THE INVENTION

1. Field of the Invention

The present invention relates generally to biocides. The present invention relates more particularly to biocidal mixtures of oxazolidine compounds and hydroxymethyl-substituted phosphorus compounds, and methods of using them.

2. Technical Background

Protecting water-based fluids (e.g., in injection and production systems) from microbial contamination is vital for the efficiency and success of any oil or natural gas production operation. Metabolic activity of microorganisms can cause microbiologically influenced corrosion (MIC) on metal surfaces of equipment and cause degradation of polymer additives. Biofilms formed by both aerobic and anaerobic bacteria can physically plug oil and gas pipelines and water purification systems, as well as reduce efficiency of pumps and heat transfer systems. Moreover, certain anaerobic bacteria, known as sulfate reducing bacteria, can reduce sulfate to produce hydrogen sulfide, which can sour oil and gas, corrode pipelines and storage tanks and cause deposits of iron sulfide. Microbial contamination can occur anywhere throughout the oil and natural gas field during oil and gas production operations. For example, although aerobic and anaerobic bacteria coexist in many environments, aerobic bacteria are more often found topside (i.e., near the surface) in injection water, produced water, and functional water-based fluids such as drilling muds, completion or workover fluids, stimulation fluids and fracturing fluids. Anaerobic bacteria, on the other hand, are most commonly found downhole (i.e., underground) in oil or gas reservoirs, near bore areas, in produced fluids, in deaeration towers, in transmission pipelines, and in the water bottoms of oil and gas storage tanks.

Biological contamination is a major complication in many other industrial processes and systems. Pulp and paper water, cooling water (e.g., in cooling towers), boiler water, industrial process water, ballast water, waste water, metalworking fluids, water-based slurry, ink and tape-joint compound, water-based household products and personal care products, latex, paint, coatings, and water purification and treatment systems and components thereof are all vulnerable to contamination by aerobic and anaerobic bacteria.

SUMMARY OF THE INVENTION

Biocides are commonly used to control the growth of microorganisms in aqueous systems. However, many are not entirely effective at controlling all types of bacterial growth and some are incompatible with other water treatment additives. The inventors have determined that there remains a need for biocidal treatment methods and formulations having increased efficiency over current systems.

One aspect of the invention is a method of reducing or inhibiting increase in the concentration of microbes in a water-based fluid or in a system used with a water-based fluid, the method comprising contacting the water-based fluid or system with an oxazolidine compound and a hydroxymethyl-substituted phosphorus compound selected from the group consisting of tetrakis(hydroxymethyl)phosphonium salts, $C_1$-$C_3$ alkyl- and alkenyltris(hydroxymethyl)phosphonium salts and tris(hydroxymethyl)phosphine.

Another aspect of the invention is a formulation for reducing or inhibiting increase in the concentration of microbes in a water-based fluid or in a system used with a water-based fluid, the formulation comprising an oxazolidine compound and a hydroxymethyl-substituted phosphorus compound selected from the group consisting of tetrakis(hydroxymethyl)phosphonium salts, $C_1$-$C_3$ alkyl- and alkenyltris(hydroxymethyl)phosphonium salts and tris(hydroxymethyl)phosphine.

The present invention is capable of providing a number of advantages over the prior art. For example, use of both an oxazolidine compound and a hydroxymethyl-substituted phosphorus compound can unexpectedly maximize synergy between the two components in a wide range of applications. The methods and formulations of the present invention can be used at relatively low biocide loadings, reducing cost, odor, worker exposure and environmental effects. In certain embodiments of the invention, the biocidal treatment can be carried out in the absence of a quaternary ammonium salt, and therefore allows the unhindered use of anionic polymers for flocculation and purification. Additional features and advantages of the invention will be set forth in the detailed description which follows and will be readily apparent to those skilled in the art from the description or recognized by practicing the invention as described in the written description and claims hereof, as well as in the appended drawings.

It is to be understood that both the foregoing general description and the following detailed description are merely exemplary of the invention, and are intended to provide an overview or framework for understanding the nature and character of the invention as it is claimed.

DETAILED DESCRIPTION OF THE INVENTION

One aspect of the invention is a method of reducing or inhibiting an increase in the concentration of microbes in a water-based fluid or in a system used with a water-based fluid. The method comprises contacting the water-based fluid or system with an oxazolidine compound and a hydroxymethyl-substituted phosphorus compound selected from the group consisting of tetrakis(hydroxymethyl)phosphonium salts, $C_1$-$C_3$ alkyl- and alkenyltris(hydroxymethyl)phosphonium salts and tris(hydroxymethyl)phosphine. As described in more detail below, the inventors have unexpectedly found that the use of hydroxymethyl-substituted phosphorus compounds and oxazolidine compounds together can provide better biocidal activity than the use of either substance alone.

Water-based fluids treatable using the methods of the present invention can be found in many forms. For example, the water-based fluid can exist as a volume of water or aqueous solution. Alternatively, the water-based fluid can be a slurry or suspension, or can be the liquid fraction of a mud, pulp, or other mixed-phase system. As the skilled artisan will appreciate, the water-based fluids treatable according to the present invention may include other substances, such as polymers, demulsifiers, corrosion inhibitors, scale inhibitors and/or surfactants. Depending on the application, the water-based fluids can also include other appropriate substances, such as thickeners (e.g., clays, polymers), salts, density increasing substances (e.g., barite), lubricants and viscosity modifiers. Similarly, systems used with water-based fluids take many forms, and include, for example, systems used in water purification, oil or natural gas production and transmission, paper- and pulpmaking, metalworking, heating and cooling, storage, and cleaning and rinsing processes.

In one embodiment of the invention, the oxazolidine compound is a monocyclic oxazolidine, bicyclic oxazolidine, bisoxazolidine, or polyoxazolidine, each of which is optionally substituted with $C_1$-$C_6$ alkyl, $C_1$-$C_6$ alkoxy, or hydroxy ($C_1$-$C_6$ alkyl).

In one embodiment, the oxazolidine compound is monocyclic oxazolidine such as 4,4-dimethyoxazolidine. 4,4-dimethyloxazolidine is available as a 78 wt % solution in water from The Dow Chemical Company as BIOBAN™ CS-1135. In another embodiment, the oxazolidine compound is bicyclic oxazolidine. For example, the oxazolidine compound can be a 1-aza-3,7-bicyclo[3.3.0]octane optionally substituted with $C_1$-$C_6$ alkyl, $C_1$-$C_6$ alkoxy, or hydroxy($C_1$-$C_6$ alkyl), such as 7-ethylbicyclooxazolidine (5-ethyl-1-aza-3,7-dioxabicyclo[3.3.0]octane), 5-hydroxymethoxymethyl-1-aza-3,7-dioxabicyclo[3.3.0]octane and 5-hydroxymethyl-1-aza-3,7-dioxabicyclo[3.3.0]octane. 7-ethyl-bicyclooxazolidine is available in 97% purity (remainder water) from The Dow Chemical Company as BIOBAN™ CS-1246, and 5-hydroxymethyl- and 5-hydroxymethoxymethyl-1-aza-3,7-dioxabicyclo[3.3.0]octane are available as a mixture as NUOSEPT® 95 from International Specialty Products. In another embodiment of the invention, the oxazolidine compound is a bisoxazolidine. For example, the bisoxazolidine N,N-methylenebis(5-methyl-oxazolidine) is available in 90-100% purity from Halliburton as STARCIDE®. In other embodiments of the invention, the oxazolidine compound is a polyoxazolidine. Of course, more than one oxazolidine compound can be combined for use in the present invention; in such cases, ratios and concentrations are calculated using the total weight of all oxazolidine compounds.

Hydroxymethyl-substituted phosphorus compounds are also generally available both in undissolved form or as aqueous solutions. In one embodiment of the invention, the hydroxymethyl-substituted phosphorus compound is a tetrakis(hydroxymethyl)phosphonium salt. For example, the hydroxymethyl-substituted phosphorus compound can be tetrakis(hydroxymethyl)phosphonium sulfate (THPS). THPS is available from The Dow Chemical Company as AQUCAR™ THPS 75, a 75 wt % solution in water. Other tetrakis(hydroxymethyl)phosphonium salts, such as tetrakis(hydroxymethyl)phosphonium chloride, can also be used. In other embodiments of the invention, the hydroxymethyl-substituted phosphorus compound is a $C_1$-$C_3$ alkyl- and alkenyl-tris(hydroxymethyl)phosphonium salt or tris(hydroxymethyl)phosphine. Of course, more than one of the recited hydroxymethyl-substituted phosphorus compounds can be combined for use in the present invention; in such cases, ratios and concentrations are calculated using the total weight of all hydroxymethyl-substituted phosphorus compounds.

In one embodiment of the invention, the weight ratio of hydroxymethyl-substituted phosphorus compound to oxazolidine compound is in the range of about 50:1 to about 1:50. In certain embodiments of the invention, the weight ratio of hydroxymethyl-substituted phosphorus compound to oxazolidine compound is in the range of about 5:1 to about 1:10. For example, the weight ratio of hydroxymethyl-substituted phosphorus compound to the oxazolidine compound can be in the range of about 5:1 to about 1:1, or in the range of about 1:5 to about 1:10. All ratios discussed herein are weight/weight, unless otherwise noted. The methods of the present invention can be used in a variety of applications to treat a wide variety of water-based fluids, such as oilfield and natural gas field water and functional fluids or components of the functional fluids (e.g. drilling muds, completion and workover fluids, stimulation fluids, packing fluids, fracturing fluids, hydrotest fluids), pulp or paper water and slurry, cooling water, boiler water, industrial process water, ballast water, waste water, metalworking fluids, hydrocarbon oil and natural gas, water-based slurry, ink and tape joint compound, water-based household products and personal care products, latex, paint and coatings. As used herein, "water-based fluid" includes hydrocarbon oil and natural gas that may have an aqueous phase associated therewith. The methods of the present invention can be especially useful in treating oilfield and natural gas field water and functional fluids, oil and gas transmission and storage systems. The methods of the present invention can also be used in a variety of systems used with water-based fluids, such as those used in heating, cooling, oil and natural gas production, paper production. The methods of the present invention can also be used to control bacteria and prevent biofouling in water purification systems, such as those using reverse osmosis membranes, microfiltration membranes or ultrafiltration membranes, as well as those using sand filtration, multimedia filtration, active carbon filtration, ion exchange and electrodionization.

In one embodiment of the invention, the microbes are aerobic bacteria. In certain embodiments of the invention, aerobic bacteria are treated using a weight ratio of hydroxymethyl-substituted phosphorus compound to oxazolidine compound in the range of about 50:1 to about 1:50. These ratios can be useful in reducing and/or maintaining microbial concentrations in water-based fluids and systems in which aerobic bacteria are dominant, such as topside or surface oil field and natural gas field water, components of oil and gas field drilling muds, completion and workover water-based fluids, stimulation fluids, packing fluids, fracturing water-based fluids, hydrotest fluids, hydrocarbon oil and gas, water-based slurry, ink and tape joint compounds, water-based household products and personal care products, latex, paint, coatings, metalworking fluids and systems, ballast water, cooling water, boiler water, pulp or paper processing systems or water-based fluids associated therewith, industrial process water, and other open systems and water-based fluids therein.

According to another embodiment of the invention, the microbes are anaerobic bacteria. In certain embodiments of the invention, anaerobic bacteria are treated using a weight ratio of hydroxymethyl-substituted phosphorus compound to oxazolidine compound in the range of about 50:1 to about 1:50. These ratios can be useful in reducing and/or maintaining microbial concentrations in water-based fluids and systems in which anaerobic bacteria are dominant, such as injection water and fluids in oil and natural gas reservoirs, produced water and fluids in oil and gas production operations, oil or gas storage tanks or water-based fluids therein, deaeration towers or water-based fluids therein, transmission pipelines or water based fluids therein, pulp or paper processing systems or water-based fluids associated therewith, ballast water, wastewater treatment systems and water-based fluids therein, and closed systems and lower parts of open systems and water-based fluids therein.

The skilled artisan can select final working concentrations of the oxazolidine compound and the hydroxymethyl-substituted phosphorus compound necessary to provide the desired antimicrobial effect. For example, according to one embodiment of the invention, the combined concentration of oxazolidine compound and hydroxymethyl-substituted phosphorus compound in the water-based fluid or system is in the range of about 5 ppm to about 3500 ppm. The combined concentration of oxazolidine compound and hydroxymethyl-substituted phosphorus compound in the water-based fluid or system can be in the range of about 10 ppm to about 500 ppm. In certain embodiments of the invention, the combined concentration of oxazolidine compound and hydroxymethyl-substituted phosphorus compound in the water-based fluid or system is in the range of about 50 ppm to about 200 ppm, or in the range of about 10 ppm to about 100 ppm. In other embodiments of the invention, the combined concentration of oxazolidine compound and hydroxymethyl-substituted phosphorus compound in the water-based fluid or system can be in the range of about 1 ppm to about 20000 ppm.

According to one embodiment of the invention, during the contacting step the water-based fluid or system is substantially free of quaternary ammonium compounds. For example, the water-based fluid or system can have less than 100 ppm, less than 25 ppm, less than 5 ppm, or even less than 1 ppm. The inventors have found ratios of hydroxymethyl-substituted phosphorus compound and oxazolidine compound that provide biocidal efficiency without the use of quaternary ammonium compounds. In this embodiment of the invention, therefore, the water-based fluid can contain at least one polymer (anionic, cationic or nonionic), demulsifier, corrosion inhibitor, scale inhibitor and/or surfactant without suffering a reduction in efficacy due to the presence of (e.g., through precipitation by) quaternary ammonium species.

In certain embodiments of the invention, during the contacting step the water-based fluid or system is substantially free of adducts between formaldehyde and $C_2$-$C_6$ aliphatic glycol or $C_2$-$C_6$ aliphatic glycol mono $C_1$-$C_4$ alkyl ether. For example, the water based fluid can have a concentration of adducts between formaldehyde and $C_2$-$C_6$ aliphatic glycol or $C_2$-$C_6$ aliphatic glycol mono $C_1$-$C_4$ alkyl ether of less than about 100 ppm, less than 25 ppm, less than 5 ppm, or even less than 1 ppm.

In certain embodiments of the invention, the method includes contacting the water-based fluid or system with at least one additional biocide. The skilled artisan will choose the identity and concentration of the additional biocide based on the particular application envisioned. Suitable additional biocides include, for example, 2,2-dibromo-2-nitrilopropionamide (DBNPA), 2-bromo-2-nitropropane-1,3-diol (bronopol), 2-methyl-4-isothiazolin-3-one (MIT), tris(hydroxymethyl)nitromethane, 1-(3-chloroallyl)-3,5,7-triaza-1-azonia-adamantane chloride, 1,2-benzisothiazolin-3-one, 2,6-dimethyl-m-dioxan-4-ol acetate, and o-phthalaldehyde.

In some embodiments of the invention, the water-based fluid or system is contacted with the oxazolidine compound and the hydroxymethyl-substituted phosphorus compound at more than one ratio of hydroxymethyl-substituted phosphorus compound to oxazolidine compound. For example, in one embodiment of the invention, the water-based fluid is contacted at a first ratio of hydroxymethyl-substituted phosphorus compound to oxazolidine compound in the range of about 50:1 to about 1:50; and also contacted at a second ratio of hydroxymethyl-substituted phosphorus compound to oxazolidine compound in the range of about 50:1 to about 1:50, in which the first ratio is different than the second ratio. The contacting at the first ratio can be performed before the contacting at the second ratio. Alternatively, the contacting at the second ratio can be performed before the contacting at the first ratio. The methods according to these embodiments of the invention can be used to reduce or prevent microbial contamination in a water-based fluid or system over time. As the skilled artisan will appreciate, as a water-based fluid moves through a system or process, or as the process taking place in a system evolves, it can be subject to contamination by different types of microbes. For example, at a position or time where the water-based fluid or system is at risk of contamination by aerobic microbes, it can be contacted at a first ratio in the range of about 50:1 to about 1:50. Similarly, at a position or time in a system or process where the water-based fluid is at risk of contamination by anaerobic microbes, it can be contacted at a second ratio in the range of about 50:1 to about 1:50. For example, water or a functional fluid is often injected downhole into an oil or gas well to enhance the productivity of the oil or gas well. The water or functional fluid can initially be contacted at a first ratio in order to achieve better control of aerobic microbes. At a later point, for example when the fresh water enters a deaeration tower and/or immediately before the water or functional fluid is injected downhole, it can be contacted at a second ratio to obtain and maintain better control of anaerobic microbes in deaeration towers and/or downhole areas. In souring wells, produced fluids can first be treated at one ratio of hydroxymethyl-substituted phosphorus compound to oxazolidine compound in order to reduce anaerobic sulfate-reducing bacteria and hydrogen sulfide. After oil/gas/water separation, the produced water can be treated with a another ratio of hydroxymethyl-substituted phosphorus compound to oxazolidine compound before release or reinjection in order to better control aerobic microbes.

The contacting can be performed in many different ways, depending on factors such as the type of water-based fluid or system being treated and its location in an oil or gas production or other industrial system or process. For example, the oxazolidine compound and the hydroxymethyl-substituted phosphorus compound can be added to the water-based fluid or system at substantially the same time. For example, the oxazolidine compound and the hydroxymethyl-substituted phosphorus compound can be provided as a mixture in the desired ratio, which is added to the water-based fluid or system. Alternatively, the oxazolidine compound can be added to the water-based fluid or system at substantially the same time by adding one after the other with little delay (i.e., 3 minutes or less) between additions. In other embodiments of the invention, the oxazolidine compound and the hydroxymethyl-substituted phosphorus compound are added to the water-based fluid or system at different times (i.e., with a delay of more than 3 minutes). In these embodiments of the invention, the oxazolidine compound and hydroxymethyl-substituted phosphorus compound components are added to yield after addition the desired final concentration and ratio in the water-based fluid or system. The oxazolidine compound and hydroxymethyl-substituted phosphorus compound may be added in a single dose (or "slug") to a pipeline, reservoir or other part of a system, or may be added together in multiple slugs. The oxazolidine compound and hydroxymethyl-substituted phosphorus compound may alternatively be continuously added to the water-based fluid or system in order to maintain a desired concentration and ratio of components. When the method is used with a system, system components can be contacted with the oxazolidine compound and the hydroxymethyl-substituted phosphorus compound in an assembled and/or operational state. System components can also be contacted with the oxazolidine compound and the hydroxymethyl-substituted phosphorus compound in a separate bath or fluid circulation system. For example, in methods of the invention used to treat a water purification system, the oxazolidine compound and the hydroxymethyl-substituted phosphorus compound can be pumped through the entire system (e.g., by adding them to the feed water while the system is on-line). A single system component (e.g., a membrane) can also be isolated or removed and separately treated with the oxazolidine compound and the hydroxymethyl-substituted phosphorus compound off-line in a feed tanker.

Another aspect of the invention is a formulation for reducing or inhibiting increase in the concentration of microbes in a water-based fluid or in a system used with a water-based fluid. The formulation includes an oxazolidine compound and a hydroxymethyl-substituted phosphorus compound selected from the group consisting of tetrakis(hydroxymethyl)phosphonium salts, $C_1$-$C_3$ alkyl- and alkenyltris(hydroxymethyl) phosphonium salts and tris(hydroxymethyl)phosphine. The weight ratio of hydroxymethyl-substituted phosphorus compound to oxazolidine compound is in the range of about 50:1 to about 1:50. For example, as described above with respect to the methods of the present invention, the weight ratio of hydroxymethyl-substituted phosphorus compound to oxazolidine compound can be in the range of about 10:1 to about 1:20; or in the range of about 1:1 to about 1:5. When the oxazolidine compound is 4,4-dimethyloxazolidine, the weight ratio of hydroxymethyl-substituted phosphorus compound can be, for example, in the range of about 1:1 to about 1:5. When the oxazolidine compound is 7-ethylbicyclooxazolidine, the weight ratio of hydroxymethyl-substituted phosphorus compound can be, for example, in the range of about 2:1 to about 1:15.

The formulation can have a wide variety of overall concentrations of oxazolidine compound and hydroxymethyl-substituted phosphorus compound. In certain embodiments of the invention, the total concentration of oxazolidine compound and hydroxymethyl-substituted phosphorus compound in the formulation is in the range of about 0.1 wt % to about 99 wt %. For example, the total concentration of oxazolidine compound and hydroxymethyl-substituted phosphorus compound in the formulation can be in the range of about 0.1 wt % to about 98 wt %, or in the range of about 15 wt % to about 90 wt %. During dosing of the aqueous system being treated, the user can dilute concentrated formulations to more appropriate end-use concentrations for a particular application (e.g., in the range of about 1 to about 3500 ppm; 5 ppm to about 1500 ppm; in the range of about 10 ppm to about 500 ppm; in the range of about 50 ppm to about 200 ppm; or in the range of about 10 ppm to about 100 ppm).

In certain embodiments of the invention, the formulation also includes water. For example, the water concentration of the formulation can be in the range of about 1 wt % to about 99 wt %; in the range of about 5 wt % to about 95 wt %; or in the range of about 50 wt % to about 85 wt %. Of course, other solvents, such as lower alcohols, glycols, glycol ethers and esters and dimethylformamide, can be used in the formulations of the present invention in addition to or in place of water.

The formulations of the present invention can be prepared using methods standard in the formulation arts. For example, it will often be convenient to simply blend commercially-available concentrated aqueous solutions (such as BIOBAN™ CS-1135 or BIOBAN™ CS-1246 solutions for the oxazolidine compound, and AQUCAR™ THPS 75 for the hydroxymethyl-substituted phosphorus compound) in proportions appropriate to yield the desired ratios. Other additives can be added as desired, and water (and/or other solvents) can be added to further dilute the formulation to a desired total concentration.

In one embodiment of the invention, the hydroxymethyl-substituted phosphorus compound is a tetrakis(hydroxymethyl)phosphonium salt. For example, the hydroxymethyl-substituted phosphorus compound can be tetrakis(hydroxymethyl)phosphonium sulfate. Of course, other tetrakis(hydroxymethyl)phosphonium salts, such as tetrakis(hydroxymethyl)phosphonium chloride, can also be used.

In certain embodiments of the invention, the formulation includes at least one additional biocide. The skilled artisan can select the identity and concentration of the additional biocide based on the particular application envisioned. Suitable additional biocides include, for example, 2,2-dibromo-2-nitrilopropionamide (DBNPA), 2-bromo-2-nitropropane-1,3-diol (bronopol), 2-methyl-4-isothiazolin-3-one (MIT), tris(hydroxymethyl)nitromethane, 1-(3-chloroallyl)-3,5,7-triaza-1-azonia-adamantane chloride, 1,2-benzisothiazolin-3-one, 2,6-dimethyl-m-dioxan-4-ol acetate, and o-phthalaldehyde.

In certain embodiments of the invention, the formulation is free or substantially free of quaternary ammonium compounds. For example, the formulation can have less than 10 wt %, less than 1 wt %, or even less than 0.25 wt % quaternary ammonium compounds. As described above, quaternary ammonium compounds can be disfavored when additives such as anionic polymers, demulsifiers, corrosion inhibitors and/or surfactants are to be used. Accordingly, in this embodiment of the invention, the formulation can include at least one charged or uncharged polymer, demulsifier, corrosion inhibitor, scale inhibitor and/or surfactant. Of course, in other embodiments of the invention, the formulation can include a quaternary ammonium compound.

In certain embodiments of the invention, the formulation is free or substantially free of adducts between formaldehyde and $C_2$-$C_6$ aliphatic glycol or $C_2$-$C_6$ aliphatic glycol (mono $C_1$-$C_4$ alkyl ether). For example, the formulation can have less than 10 wt %, less than 1 wt %, or even less than 0.25 wt % adducts between formaldehyde and $C_2$-$C_6$ aliphatic glycol or $C_2$-$C_6$ aliphatic glycol (mono $C_1$-$C_4$ alkyl ether).

The formulations of the present invention can include other substances, depending on the ultimate application. However, in one embodiment of the invention the formulations consist essentially of the oxazolidine compound, the hydroxymethyl-substituted phosphorus compound, and water.

Other aspects of the invention include embodiments that combine not inconsistent aspects from one or more of the embodiments described above. For example, one embodiment described above uses THPS as the hydroxymethyl-substituted phosphorus compound, and another embodiment described above the system being treated is free of quaternary ammonium compounds. Accordingly, in yet another embodiment of the invention, the hydroxymethyl-substituted phosphorus compound is THPS and the system being treated is free of quaternary ammonium compounds.

The methods and formulations of the present invention can be adapted for use in many applications. For example, the methods and formulations of the present invention can be used in many phases of oil or natural gas production, transmission, and storage, both topside and downhole, such as in deaeration towers, storage tanks, injection water, production water, pigging operations, drilling muds, completion or workover fluids, stimulation fluids, packing fluids, fracturing fluids and hydrotest fluids. The methods and formulations can be used in water treatment and purification processes and systems, for example to treat membranes and other system components that are susceptible to fouling. The methods and formulations can also be used in paper and pulp production, ballast water disinfection and in other industrial processes. The methods and formulations can help prevent microbial contamination of water-based fluids and systems used in cooling and heating processes. The methods and formulations can also be used to prevent microbial contamination of water-based slurry, ink and tape-joint compound, water-based household products and personal care products, latex, paint and coatings. Of course, the methods and formulations of the present invention can also be used in other processes and apparati not mentioned specifically herein.

EXAMPLES

Example 1

Activity of 4,4-dimethyloxazolidine and THPS Against Various Bacteria

A sterile 0.85% NaCl solution is contaminated with bacterial inoculums at final bacterial concentrations of ~$10^7$ CFU/mL. At day zero, either oxazolidine compound (BIOBAN™ CS-1135, 78% 4,4-dimethyloxazolidine in water, The Dow Chemical Company, or BIOBAN™ CS-1246, 97.5% 7-ethylbicyclooxazolidine in water, The Dow Chemical Company), THPS (AQUCAR™ THPS 75, 75% THPS in water, The Dow Chemical Company), or a combination of oxazolidine compound and THPS is added and the solution mixed well to provide a desired final concentration. The solution is then incubated at 37° C. for 3 hours. The number of live bacteria in the solution after 3 hour treatment is determined using a serial dilution method.

The testing protocol described above is used for the standard bacterial strains *Staphylococcus aureus* ATCC 6538, *Klebsiella pneumoniae* ATCC 8308, *Bacillus subtillus* ATCC 8473, *Escherichia coli* ATCC 11229. Table 1 shows the average concentrations needed to achieve at least 3 log bacterial reduction in 1 hour for four bacteria (treatment alone or at a 1:1 ratio of THPS to 4,4-dimethyloxazolidine).

TABLE 1

| Biocides | | Concentration required to achieve at least 3 log bacterial reduction in 1 hr (ppm, active) |
|---|---|---|
| THPS alone | | 44.49 |
| Blend at ratio of 1:1 (active weight) | THPS | 17.24 |
|  | 4,4-dimethyl-oxazolidine | 17.24 |
| 4,4-dimethyloxazolidine alone | | 272.04 |

The protocol used to test against oil/gas field-isolated sulfate reducing bacteria (SRB) is performed as described above, but under anaerobic environment (Bactron III anaerobic chamber) and using a deaerated sterile salt solution (1.2490 g NaCl, 2.9290 g NaHCO$_3$, 0.1910 g Na$_2$CO$_3$, 0.0060 g Na$_2$SO$_4$, 0.033 g CaCl$_2$, and 0.0590 g MgCl$_2$.6H2O in 1 L water) instead of 0.85% NaCl solution. Table 2 shows the average concentrations needed to achieve at least 3 log bacterial reduction in 1 hour for oil/gas field isolated sulfate-reducing bacteria (treatment alone or at a 1:2 and 1:5 ratios of TIPS to 4,4-dimethyl-oxazolidine).

TABLE 2

| Biocides | | Concentration required to achieve at least 3 log bacterial reduction in 1 hr (ppm, active) |
|---|---|---|
| THPS alone | | 33.35 |
| 4,4-dimethyloxazolidine alone | | 1000 |

TABLE 2-continued

| Biocides | | Concentration required to achieve at least 3 log bacterial reduction in 1 hr (ppm, active) |
|---|---|---|
| Blend at ratio of 1:2 (active weight) | THPS | 18.54 |
|  | 4,4-dimethyl-oxazolidine | 37.08 |
| Blend at weight ratio of 1:5 (active weight) | THPS | 14.83 |
|  | 4,4-dimethyl-oxazolidine | 74.16 |

Example 2

Activity of 7-ethyl-bicyclooxazolidine, and THPS Against Various Bacteria

The testing protocol described in Example 1 is used for aerobic bacteria and anaerobic sulfate reducing bacteria. Table 3 shows the average concentrations needed to achieve at least 3 log bacterial reduction in 1 hour for standard aerobic bacteria and for oil/gas field isolated sulfate reducing bacteria (treatment with THPS/7-ethyl-bicyclooxazolidine blend, THPS alone, or 7-ethyl-bicyclooxazolidine alone).

TABLE 3

| Biocides | | Concentration required to achieve at lease 3 log bacterial reduction in 1 hr (ppm, active) | |
|---|---|---|---|
|  |  | Standard aerobic bacteria | Field anaerobic SRB |
| THPS alone | | 44.49 | 33.35 |
| 7-ethylbicyclooxazolidine alone | | 272.04 | >1000 |
| Blend at weight ratio of 1:5 (active weight) | THPS | 13.75 | 14.83 |
|  | 7-ethyl-bicyclooxazolidine | 68.71 | 74.16 |

It will be apparent to those skilled in the art that various modifications and variations can be made to the present invention without departing from the scope of the invention. Thus, it is intended that the present invention cover the modifications and variations of this invention provided they come within the scope of the appended claims and their equivalents.

What is claimed is:

1. A synergistic formulation for reducing or inhibiting increase in the concentration of microbes in a water-based fluid or a system used with a water-based fluid, the formulation comprising
    an oxazolidine compound and
    a hydroxymethyl-substituted phosphorus compound selected from the group consisting of tetrakis(hydroxymethyl)phosphonium salts, $C_1$-$C_3$ alkyl- and alkenyltris(hydroxymethyl)phosphonium salts and tris(hydroxymethyl)phosphine;
wherein the ratio of hydroxymethyl-substituted phosphorus compound to oxazolidine compound is in the range of 1:1 to 1:5.

2. The formulation of claim 1, further comprising water.

3. The formulation of claim 1, wherein the oxazolidine compound is 4,4-dimethyloxazolidine or 7-ethyl-bicyclooxazolidine.

4. The formulation of claim 1, wherein the formulation includes at least one charged or uncharged polymer, demulsifier, corrosion inhibitor, scale inhibitor and/or surfactant.

5. The formulation of claim 3, wherein the oxazolidine compound is 4,4-dimethyloxazolidine.

6. The formulation of claim 1, wherein the hydroxymethyl-substituted phosphorus compound is tetrakis(hydroxymethyl)phosphonium sulfate.

7. A method of reducing or inhibiting increase in the concentration of microbes in a water-based fluid, the method comprising:
contacting the water-based fluid with the formulation of claim 1.

8. The method of claim 7, wherein the hydroxymethyl-substituted phosphorus compound is tetrakis(hydroxymethyl)phosphonium sulfate.

9. The method of claim 7, wherein the oxazolidine compound is a monocyclic oxazolidine optionally substituted with $C_1$-$C_6$ alkyl, $C_1$-$C_6$ alkoxy, or hydroxy($C_1$-$C_6$ alkyl).

10. The method of claim 7, wherein the oxazolidine compound is 4,4-dimethyl-oxazolidine.

11. The method of claim 7, wherein the oxazolidine compound is a bicyclic oxazolidine optionally substituted with $C_1$-$C_6$ alkyl, $C_1$-$C_6$ alkoxy, or hydroxy($C_1$-$C_6$ alkyl).

12. The method of claim 11, wherein the oxazolidine compound is 7-ethyl-bicyclooxazolidine.

13. The method of claim 7, wherein the water-based fluid is oilfield or natural gas field water or fluid, hydrocarbon oil and gas, pulp or paper water or slurry, cooling water, boiler water, industrial process water, ballast water, waste water, a metal-working fluid, a water-based slurry, an ink or tape-joint compound, a water-based household product or personal care product, latex, paint, a coating, or a system used therewith.

14. The method of claim 7, wherein the combined concentration of oxazolidine compound and hydroxymethyl-substituted phosphorus compound in the water-based fluid is in the range of about 10 ppm to about 500 ppm.

15. The method of claim 7, wherein during the contacting step, the water-based fluid includes at least one charged or uncharged polymer, demulsifier, corrosion inhibitor, scale inhibitor and/or surfactant.

16. The method of claim 7, wherein the oxazolidine compound and hydroxymethyl-substituted phosphorus compound are added to the water-based fluid at substantially the same time.

17. The method of claim 7, wherein the contacting comprises:
contacting the water-based fluid with the oxazolidine compound and the hydroxymethyl-substituted phosphorus compound at a first ratio of hydroxymethyl-substituted phosphorus compound to oxazolidine compound in the range of about 1:1 to 1:5; and
contacting the water-based fluid with the oxazolidine compound and the hydroxymethyl-substituted phosphorus compound at a second ratio of hydroxymethyl-substituted phosphorus compound to oxazolidine compound in the range of about 1:1 to 1:5,
wherein the first ratio is different than the second ratio.

* * * * *